United States Patent
Shi et al.

(10) Patent No.: US 11,174,266 B2
(45) Date of Patent: Nov. 16, 2021

(54) EFFICIENT PROCESS FOR THE PREPARATION OF SITAGLIPTIN

(71) Applicant: F.I.S.—FABBRICA ITALIANA SINTETICI S.P.A., Montecchio Maggiore (IT)

(72) Inventors: Terry Shi, Zhejiang (CN); Sam Lou, Zhejiang (CN); Ottorino De Lucchi, Montecchio Maggiore (IT); Pierluigi Padovan, Montecchio Maggiore (IT)

(73) Assignee: F.I.S.—FABBRICA ITALIANA SINTETICI S.P.A., Montecchio Maggiore (IT)

( * ) Notice: Subject to any disclaimer, the term of this patent is extended or adjusted under 35 U.S.C. 154(b) by 0 days.

(21) Appl. No.: 16/963,600

(22) PCT Filed: Jan. 11, 2019

(86) PCT No.: PCT/EP2019/050674
§ 371 (c)(1),
(2) Date: Jul. 21, 2020

(87) PCT Pub. No.: WO2019/158285
PCT Pub. Date: Aug. 22, 2019

(65) Prior Publication Data
US 2021/0061808 A1    Mar. 4, 2021

(30) Foreign Application Priority Data
Feb. 13, 2018 (EP) .................... 18156454

(51) Int. Cl.
*C07D 487/04* (2006.01)
*B01J 27/08* (2006.01)
*C12P 17/16* (2006.01)

(52) U.S. Cl.
CPC ............ *C07D 487/04* (2013.01); *B01J 27/08* (2013.01); *C12P 17/165* (2013.01)

(58) Field of Classification Search
CPC .................................................. C07D 487/04
USPC ....................................................... 544/350
See application file for complete search history.

(56) References Cited

U.S. PATENT DOCUMENTS

| 5,939,560 | A  | 8/1999 | Jenkins et al. |
| 2004/0068141 | A1 | 4/2004 | Armstrong et al. |
| 2004/0077901 | A1 | 4/2004 | Ikemoto et al. |

FOREIGN PATENT DOCUMENTS

| EP | 1316613 A2 | 6/2003 |
| WO | 9740832 A1 | 11/1997 |
| WO | 9819998 A2 | 5/1998 |
| WO | 2015162506 A1 | 10/2015 |

OTHER PUBLICATIONS

Milne, Journal of Organic Chemistry, 76(22), 9519-9524; 2011.*
"Chemical Abstracts Service", Database Registry [Online], 2017, XP002780193, Database accession No. 2091697-40-2, 1 page.
"Chemical Abstracts Service", Database Registry [Online], 2015, XP002780194, Database accession No. 1702443-94-4, 1 page.
International Search Report and Written Opinion for Corresponding International Application No. PCT/EP2019/050674 (10 Pages) (dated Mar. 1, 2019).

* cited by examiner

*Primary Examiner* — Nizal S Chandrakumar
(74) *Attorney, Agent, or Firm* — Lucas & Mercanti, LLP

(57) ABSTRACT

Object of the present invention is an efficient process for the preparation of the active pharmaceutical ingredient Sitagliptine and the 2,4,5-trifluorophenylacetic acid (TFAA) and salt thereof, which is a key intermediate for the synthesis of Sitagliptine.

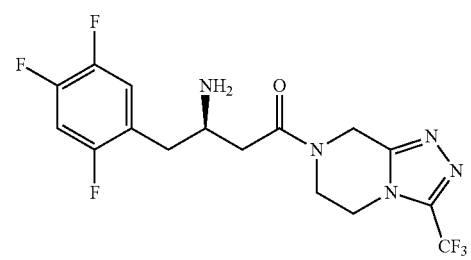

(I)

12 Claims, No Drawings

EFFICIENT PROCESS FOR THE PREPARATION OF SITAGLIPTIN

CROSS-REFERENCE TO RELATED APPLICATIONS

This application is a 371 of PCT/EP2019/050674, filed Jan. 11, 2019, which claims the benefit of European Patent Application No. 18156454.3, filed Feb. 13, 2018.

TECHNICAL FIELD

The present invention relates to a new process for the preparation of the active pharmaceutical ingredient named Sitagliptin, and to an efficient process for preparing the key intermediate named 2,4,5-trifluorophenylacetic acid.

BACKGROUND ART

The active pharmaceutical ingredient Sitagliptin of formula (I):

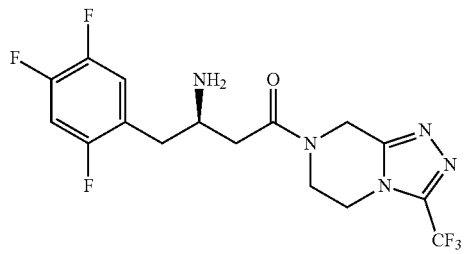

is a substance also known as MK-0431 and has chemical name 7-[(3R)-3-amino-1-oxo-4-(2,4,5-trifluorophenyl)butyl]-5,6,7,8-tetrahydro-3-(trifluoromethyl)-1,2,4-triazolo[4,3-a]pyrazine and CAS RN 486460-32-6.

This active pharmaceutical ingredient is an oral antihyperglycemic (antidiabetic drug) of the dipeptidyl peptidase-4 (DPP-4) inhibitor. This enzyme-inhibiting drug is used alone or in combination with other oral antihyperglycemic agents, such as for example metformin or a thiazolidinedione, for treatment of diabetes mellitus type 2. The benefit of this medicine is its fewer side effects (e.g. less hypoglycemia, less weight gain) in the control of blood glucose values.

The inhibitors of the dipeptidyl peptidase-4 enzyme are medicines useful in treating diabetes, in particular type 2 diabetes (see for example WO97/40832; WO98/19998; U.S. Pat. No. 5,939,560; Bioorg. Med. Chem. Lett., 6, 1163-1166 (1996); Bioorg. Med. Chem. Lett., 6, 2745-2748 (1996)).

Sitagliptin is a successful active pharmaceutical ingredient with a very high economical turnover.

Sitagliptin is commercially available as the phosphate salt monohydrate, which has CAS RN 654671-77-9, and it is sold as pharmaceutical product under the trade name Januvia®.

Considering the commercial interest for Sitagliptin, many methods for the preparation of said compound have been developed, many of them being addressed to minimize the production costs of said compound.

In particular, according to the knowledge of the Applicant, at the moment have been described about 60 different route of synthesis directed to Sitagliptin and intermediates thereof, part of them described in about 300 patent families directed to them.

Within said very large number synthetic approaches for the preparation of Sitagliptin, each one comprising many steps and many different intermediates, the Applicant's attention has been focused on the methods which involve the intermediate compound named 2,4,5-trifluorophenylacetic acid (abbreviated TFPAA) having the following chemical formula (II):

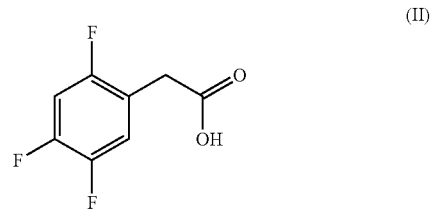 [SMILES: O=C(O)Cc1cc(F)c(F)cc1F]

and having chemical name 2,4,5-trifluorobenzeneacetic acid.

In literature have been described many method for preparing TFPAA.

In the following pages the most interesting of them have been briefly described.

In particular, US2004/0068141A1 describes a process for the preparation of fluorophenylacetic acids starting from aromatic halides according to the method described in scheme 1 wherein X represents chlorine, bromine or iodine:

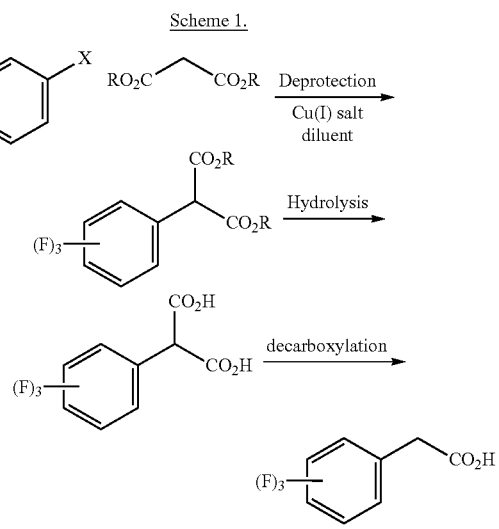

The first step however requires the use of large quantities of copper salts, with related problems of extraction and disposal of the toxic heavy metal, and the aromatic halide used often has high costs.

U.S. application number US2004/077901 describes a process for the preparation TFPAA starting from 1,2,4,5-halo benzene according to the method described in scheme 2:

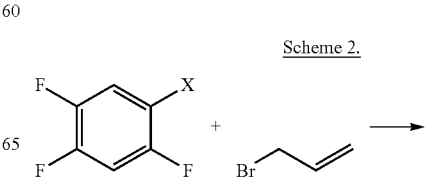

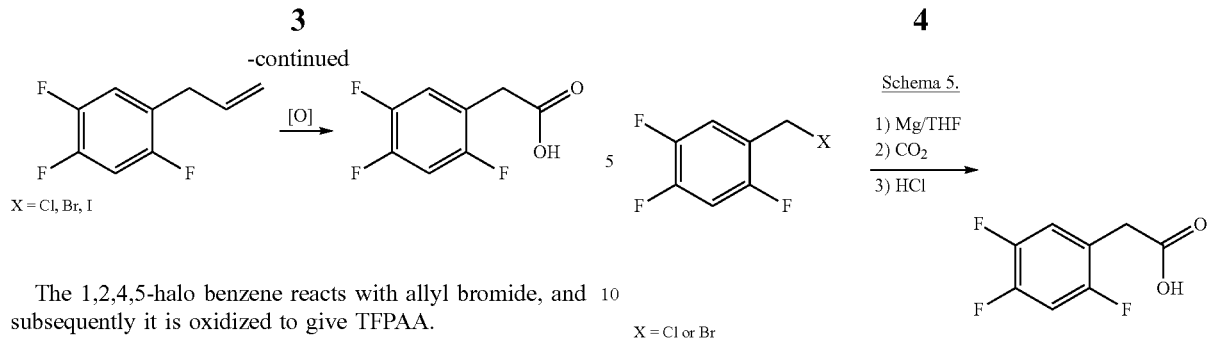

The 1,2,4,5-halo benzene reacts with allyl bromide, and subsequently it is oxidized to give TFPAA.

That synthetic route however requires the use of expensive starting materials, and the relatively harsh reaction conditions which make this method not suitable for industrial production.

Chinese patent CN1749232 describes a three-steps process for the preparation TFPAA starting from 1,2,4-trifluorobenzene according to the following scheme 3:

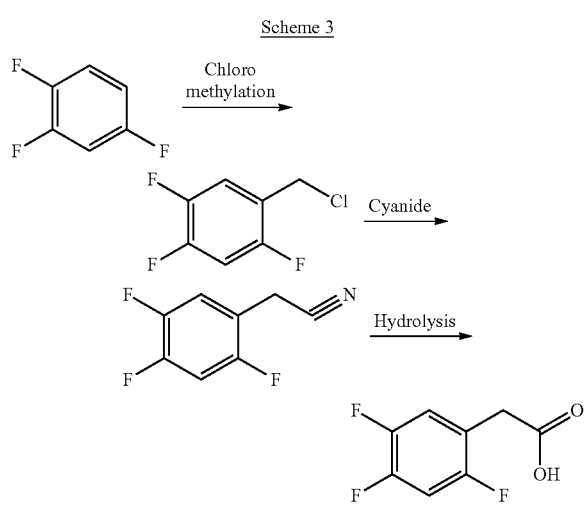

However, the synthesis requires the use of cyanides which is a very toxic reagent.

Chinese patent CN101092345 describes a two-steps process for the preparation of TFPAA starting from 1,2,4-fluorobenzene, according to the following scheme 4:

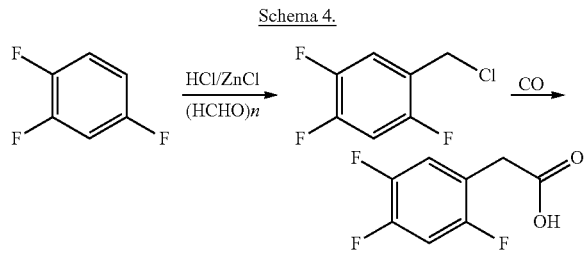

However, the carbonylation reaction is difficult and requires the use of monoxide of carbon which is a toxic gas.

Chinese patents CN101823952 and CN101429115, describes a process for the preparation of TFPAA starting from the intermediate 2,4,5-trifluorobenzyl chloride or bromide, according to the following scheme 5:

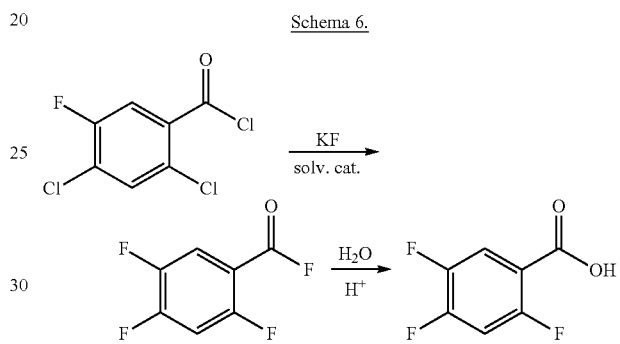

Chinese patent CN1328238 describes a two-steps process for the preparation of 2,4,5-trifluorobenzoic acid starting from 2,4-dichloro-5-fluorobenzoyl chloride, according to the following scheme 6:

Moreover, an optimized fluorination process for obtaining of 2,4,5-trifluorobenzoic acid was described in EP 0673912.

Within many synthetic approaches for the preparation of TFPAA, each one comprising many steps and many intermediates, the Applicant, willing to improve the synthesis of Sitagliptin, tried to find a more efficient synthesis of TFPAA.

The prior art methods for the synthesis of TFPAA indeed suffer of the drawbacks that the numbers of step is generally high, by the use of hazardous reagents or because they require dedicated special industrial apparatus or, finally, because the overall molar yield is relatively low.

SUMMARY OF INVENTION

The problem addressed by the present invention, in the light of the prior art methods, is therefore that of providing a much more efficient process for the preparation of Sitagliptin, which also avoids the use of toxic reagents.

Another linked problem is provide an cost-effective process for the preparation of Sitagliptin.

These problems are solved by a process for the preparation of Sitagliptin and salts thereof as outlined in the annexed claims, whose definitions are integral part of the present description.

Particularly, the present invention provides an efficient and cost-effective process for the preparation of Sitagliptin.

Further features and advantages of the process according to the invention will result from the description hereafter reported of examples of realization of the invention, provided as an indication of the invention.

DESCRIPTION OF EMBODIMENTS

The object of the present invention is a process for the preparation of Sitagliptin of formula (I) or salt thereof:

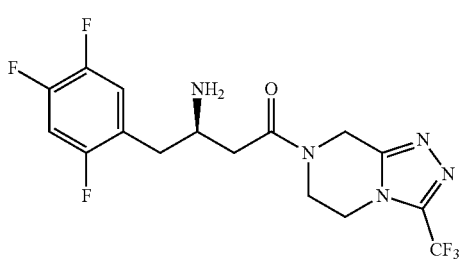
(I)

comprising of the following steps:

A) cyanation of 2,4,5-trifluorobenzoyl fluoride of formula (III):

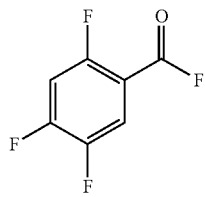
(III)

to give the compound of formula (IV):

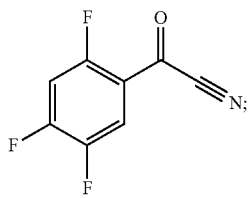
(IV)

B) conversion of the compound of formula (IV) prepared in the step A) to the compound of formula (V):

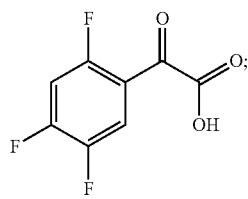
(V)

C) reduction of the compound of formula (V) prepared in the step B) to the compound of formula (II):

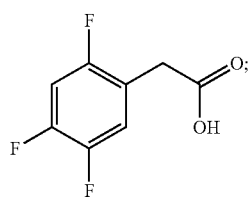
(II)

D) conversion of 2,4,5-trifluorophenylacetic acid of formula (II) obtained in the step C) to Sitagliptin of formula (I) or salt thereof.

It has indeed surprisingly found that it is possible to carry out the conversion of 2,4,5-trifluorobenzoyl fluoride of formula (III) to 2,4,5-trifluorophenylacetic acid of formula (II) (abbreviated TFPAA).

Differently from the prior art processes, it has indeed surprisingly found that it is possible to carry out the direct conversion of 2,4,5-trifluoromphenyl-oxoacetic acid of formula (V) to 2,4,5-trifluorophenylacetic acid of formula (II) (abbreviated TFPAA).

The direct conversion of 2,4,5-trifluoromphenyl-oxoacetic acid to TFPAA is carried out by means of a reduction reaction.

Although, it would be expected that in the reaction conditions wherein the oxo group is reduced also the aromatic ring would be hydrodefluorinated, the process of the invention instead provides as product TFPAA, i.e. the potentially competing hydrodefluorination reaction does not occur.

According to the invention, the process for the preparation of Sitagliptin of formula (I) and salt thereof, comprises also the step D) which is carried out by means of the following steps:

E) the conversion of 2,4,5-trifluorophenylacetic acid of formula (II) obtained in the step C) to Ketoamide of formula (VI):

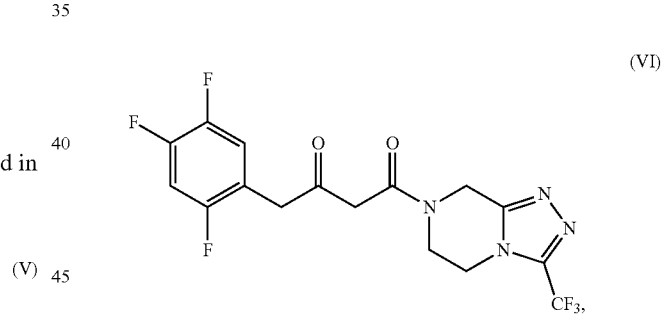
(VI)

F) the amination reaction of Ketoamide of formula (VI) produced in the step E) to give Enamine Amide of formula (VII):

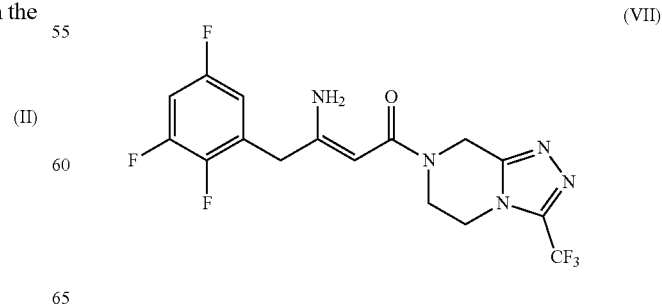
(VII)

G) the conversion of Enamine Amide of formula (VII) obtained in the step F) to Sitagliptin of formula (I):

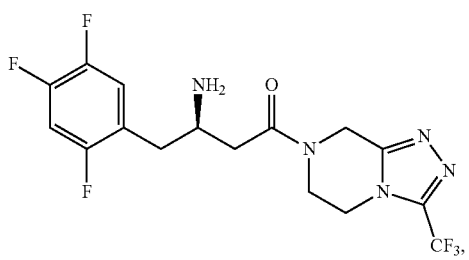
(I)

or by means the alternative process for obtaining Sitagliptin, wherein the steps F) and G) are substituted by the following step:

D1) the enzymatic conversion of Ketoamide of formula (VI), obtained by previous step E), to Sitagliptin of formula (I):

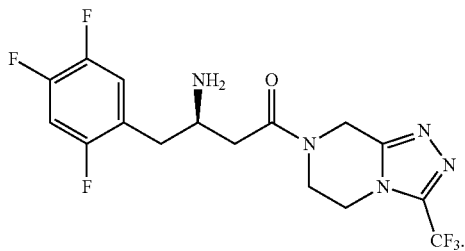
(I)

In particular, the Ketoamide compound of formula (VI) of the step E) is produced starting from TFPAA according to the known prior art methods, such as, for instance, those disclosed in WO2005/020920, purposely in the Step A of example 1 at pag. 12 and 13, which refers to scheme 2 of the example 1 at pag. 11 and 12.

In particular the step E) can be carried out firstly by reaction of TFPAA with Meldrum's acid, in presence of 4-(dimethylamino)pyridine, N,N-diisopropylethylamine and pivaloyl chloride. The intermediate compound thus prepared of formula:

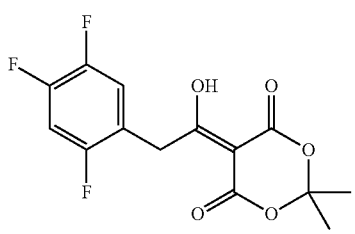 [SMILES: CC1(C)OC(=O)C(=C(O)Cc2cc(F)c(F)cc2F)C(=O)O1]

is then reacted with Triazole compound, as hydrochloride salt, of formula:

to provide the Ketoamide of formula (VI).

In the following step of the process, i.e. in the step F), the Ketoamide of formula (IV) produced in the step E) is converted into Enamine Amide of formula (V). Said conversion can be carried out, for instance, according the teaching of WO2007/050485, in particular the Step B at pag. 35 which refers to scheme 2 at pag. 34. In particular, in the step F), the Ketoamide of formula (IV) is reacted with ammonium acetate and ammonium hydroxide to provide the Enamina Amide of formula (V).

The step of conversion of Enamine Amide of formula (V) produced in the step F) to Sitagliptin of formula (I) can be carried out, for instance, according to the teaching of WO2007/050485, in particular the Step C at pag. 35 which refers to scheme 2 at pag. 34. In particular, the Enamina Amide of formula (V) is converted to Sitagliptin of formula (I) by asymmetric hydrogenation catalized by a Rodium catalyst, more particularly a catalyst comprising Rodium and Josiphos as ligand.

The alternative process for obtaining Sitagliptin by the step D1), starting from Ketoamide of formula (IV) beforehand described, consists in the enzymatic conversion of said Ketoamide obtained in the step E) to Sitagliptin of formula (I). This enzymatic conversion is described by C. K. Savile at al., in the article Science, 2010, volume 329, pag. 305-309. In particular, the Ketoamide compound of formula (IV) can be converted to Sitagliptin by means of a transaminase enzyme in presence of isopropylamine. Savile at al., also disclose improved conditions to perform the conversion of the step D1).

The process of the present invention, can also comprise the following previous step for the preparation of the compound of formula (III):

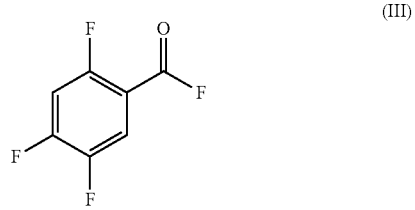 [SMILES: O=C(F)c1cc(F)c(F)cc1F]
(III)

wherein said previous step is the following step:

A-1) fluorination of the 2,4-dichloro-5-fluorobenzoyl chloride of formula (VIII):

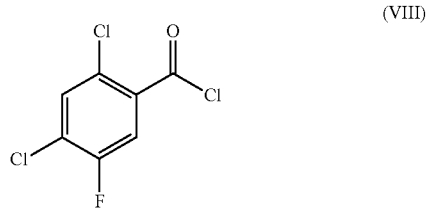 [SMILES: O=C(Cl)c1cc(F)c(Cl)cc1Cl]
(VIII)

to give the compound of formula (III):

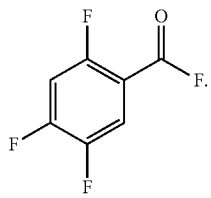

Thus, considering the steps A-1), A), B) and C), starting from 2,4-dichloro-5-fluorobenzoyl chloride, the process for the preparation of TFPAA of formula (II) consists in only four steps.

The process for obtaining the compound of formula (III) beforehand described, starting from 2,4-dichloro-5-fluorobenzoyl chloride of formula (VIII), consists in the step A-1) of fluorination of said compound (VIII), to obtain the compound of formula (III).

The fluorination reaction of the step A-1) can be carried out in presence of crown ether.

The crown ether that can be used to carry out the step A-1) of the process of the present invention can be selected in the group comprising of 12-crown-4, 15-crown-5, 18-crown-6, dibenzo-18-crown-6, and diaza-18-crown-6.

According to the preferred embodiment, the crown ether is 18-crown-6.

The step A-1) of fluorination of 2,4-dichloro-5-fluorobenzoyl chloride is carried out in presence of a fluorine source, such as, for instance KF.

The solvent used in the step A-1) can be selected in the group consisting of o-dichlorobenzene, sulfolane. According to a preferred embodiment, the step A-1) is carried out by means of o-dichlorobenzene.

In preferred embodiments, step A-1) can be conducted at a temperature between 120° C. and 150° C. More preferably, the temperature in step A-1) is comprised between 135° C. and 145° C. More preferably, the temperature in step A-1) is 140° C.

The typical molar yield of the step A-1) is comprised from 76% to 80%, and typically around 78%. The product 2,4,5-trifluorobenzoyl fluoride of formula (III) has 98-99% chemical purity by GC A/A %. The product 2,4,5-trifluorobenzoyl fluoride is an oil.

Optionally, the 2,4,5-trifluorobenzoyl fluoride of formula (III) obtained in the step A-1) can be purified by distillation.

In particular, the 2,4,5-trifluorobenzoyl fluoride of formula (III) of the step A-1) is produced starting from 2,4-dichloro-5-fluorobenzoyl chloride also according to the known prior art methods, such as, for instance, those described in CN1328238 in the example 1, and described in EP 0673912 in the example 1 or 2.

The step A) of the process of the present invention, consists in the following step for the preparation of the compound of formula (IV):

A) cyanation of 2,4,5-trifluorobenzoyl fluoride of formula (III):

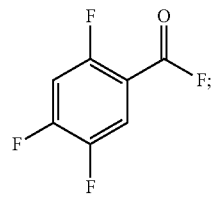

to give the compound of formula (IV):

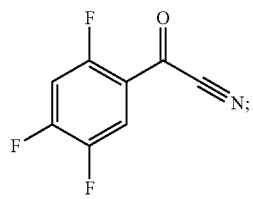

The step A) of the conversion of the compound of formula (III) to the compound of formula (IV) can be thus carried out by a cyanation reaction.

The cyanation reaction of the step A) is carried out in presence of a cyanide source. Said acid can be selected in the group comprising sodium cyanide, potassium cyanide, lithium cyanide, ammonium cyanide, organic cyanide.

According to the preferred embodiment, cyanation reaction of the step A) can be carried out in presence of sodium cyanide.

The step A) of the process according to the invention can be carried out in the presence of one or more organic solvents such as, for example, toluene, xylene, halogenated solvents, chlorobenzene, o-dichlorobenzene, tetrahydrofuran (THF), dioxane, methyl-t-butyl ether (MTBE), diethyl ether.

Preferably the reaction can be carried out in aromatic solvent or an ether solvent such as toluene, xylene, MTBE, dioxane, methyl-tetrahydrofuran (Me-THF), THF, chlorobenzene, o-dichlorobenzene, being more preferred THF, chlorobenzene and o-dichlorobenzene.

Optionally, the solution of 2,4,5-trifluorobenzoyl fluoride of formula (III) obtained in the step A-1) can be submitted directly, without isolation of compound (III), to the step A).

The molar yield of the step A) is typically from about 70% to about 90%. The product 2,4,5-trifluorobenzene-1-carbonyl cyanide of formula (IV) has 95-99% chemical purity by GC NA %. The product 2,4,5-trifluorobenzene-1-carbonyl cyanide is an oil.

The step B) of the process of the present invention, is carried out by means of the conversion of the compound of formula (IV):

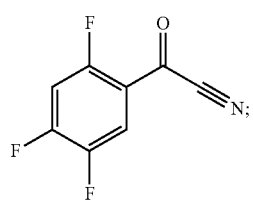

to compound of formula (V):

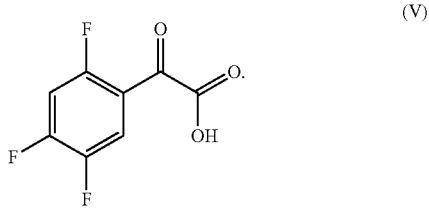

The step B) can comprise the following steps:
B1) oxidation of the 2,4,5-trifluorobenzene-1-carbonyl cyanide of formula (IV) to the compound of formula (IX):

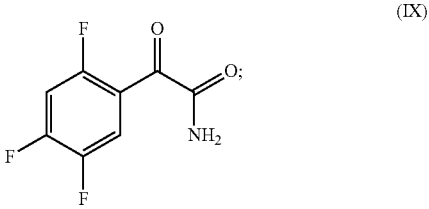 [SMILES: NC(=O)C(=O)c1cc(F)c(F)cc1F]

B2) hydrolysis of the compound of formula (IX) obtained in the step B1) to the compound of formula (VI):

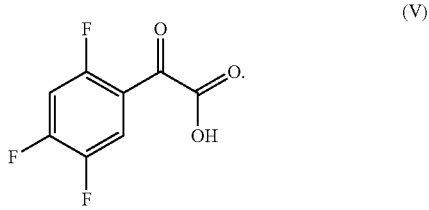

The step B) of the conversion of the compound of formula (IV) to the compound of formula (V) can be thus carried out by:
a oxidation reaction in the step B1);
an hydrolysis reaction in the step B2).

The oxidation reaction of the step B1) can be carried out in presence of alkali metal halide.

The alkali metal halide that can be used to carry out the step B1) of process of the present invention can be selected in the group comprising of sodium halide, potassium halide, lithium halide.

The alkali metal halide that can be used to carry out the step B1) of process of the present invention can be selected in the group comprising of sodium chloride, sodium bromide, sodium iodide, potassium chloride, potassium bromide, potassium iodide, lithium chloride, lithium bromide.

According to the preferred embodiment, alkali metal halide is sodium chloride or sodium bromide. More preferably, sodium chloride since it is the alkali metal halide that provide the higher reaction rate, i.e. allows the end of the conversion reaction in the shortest time.

The step B1) of the process according to the invention can be carried out in an acid solvent or an aqueous acid mixture thereof.

The acid solvent or an aqueous acid mixture thereof is sulphuric acid or a aqueous solution of sulphuric acid.

The step B2) of the process according to the invention can be carried out in an acid solvent or an aqueous acid mixture thereof.

The acid solvent or an aqueous acid mixture thereof that can be used to carry out the step B2) of the process of the present invention can be selected in the group comprising of phosphoric acid, sulphuric acid, chloridic acid, bromidic, acid, or a aqueous solution of thereof.

According to the preferred embodiment, acid solvent or an aqueous acid since it is the acid solvent or an aqueous acid mixture thereof that provide the higher reaction rate, i.e. allows the end of the conversion reaction in the shortest time.

The acid solvent or an aqueous acid mixture thereof is chloridric acid or a aqueous solution of chloridric acid.

The step B1) and B2) can be preferably carried out consequently without to isolate the compound of formula (IX).

The typical molar yield of the step B1) and B2) combined and carried out sequentially, i.e. without to isolate the compound of formula (IX), is typically from about 75% to about 85%. The product (2,4,5-trifluorophenyl)oxoacetic acid of formula (V) has 98-99% chemical purity by HPLC NA %.

The compound of formula (V) is a crystalline solid.

In the step C) of the present invention, the compound (2,4,5-trifluorophenyl)oxoacetic acid of formula (V):

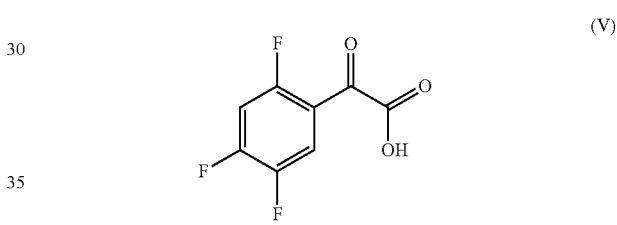

is directly converted into 2,4,5-trifluorophenylacetic acid of formula (II) or salt thereof:

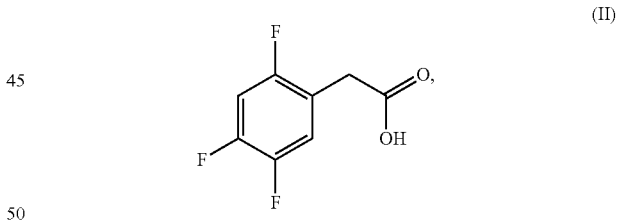

i.e. without the formation of other intermediates.

The step C) of direct conversion of the compound of formula (V) to the compound of formula (II) is carried out by a reduction reaction.

The stoichiometry of said reduction reaction foresees the addition of 4 atoms of hydrogen and the formation, as by-product, of water.

The reduction reaction of the step C) is carried out in presence of iodide catalyst.

The iodide catalyst that can be used to carry out the step C) of process of the present invention can be selected in the group comprising of iodine, sodium iodide, potassium iodide, hydroiodic acid, lithium iodide, ammonium iodide.

The amount of Iodide catalyst that can be used to carry out the step C) ranges between 0.05 and 0.5 molar equivalents compared to the starting compound of formula (V).

According to a preferred embodiment, to carry out the step C) from 0.05 to 0.2 molar equivalents of Iodide catalyst are used.

According to a more preferred embodiment, to carry out the step C) 0.1 molar equivalents of iodine as Iodide catalyst are used.

The reduction reaction of the step C) is carried out in presence in presence of a phosphorus and/or sulphurous reductant.

The phosphorus and/or sulphurous reductant that can be used to carry out the step C) of the process of the present invention can be selected in the group comprising of phosphorous acid, hypophosphorous acid, pyrophosphoric acid, triphosphoric acid, trimethaphosphoric acid, hypophosphoric acid, red phosphorus, sulfurous acid, pyrosulfurous acid, peroxymonosulfuric acid, hyposulfurous acid.

According to the preferred embodiment, the phosphorus and/or sulphurous reductant is phosphorous acid.

The amount of phosphorus and/or sulphurous reductant that can be used to carry out the step C) ranges between 1.5 and 8 molar equivalents compared to the starting compound of formula (V).

According to a preferred embodiment, to carry out the step C) from 3 to 6 molar equivalents of phosphorus and/or sulphurous reductant are used.

According to a more preferred embodiment, to carry out the step C) 4 molar equivalents of phosphorous acid as phosphorus and/or sulphurous reductant are used.

The step C) of process of the present invention can be carried out in presence of an acid or an aqueous acid mixture thereof.

The acid or an aqueous acid mixture thereof to carry out step C) can be chosen in the group comprising of hydroiodic acid, hydrobromic acid, acetic acid, methansulphonic acid, trifluoromethansulphonic acid.

According to preferred embodiment, the acid or an aqueous acid mixture thereof can be chosen in the group comprising of hydrobromic acid, acetic and methansulphonic acid.

According to a more preferred embodiment, the acid or an aqueous acid mixture thereof is methansulphonic acid since it is the acid that provides the higher reaction rate, i.e. allows the end of the reduction reaction in the shortest time.

According to the preferred embodiment, the acid or an aqueous acid mixture thereof can be an aqueous acid mixture thereof. Examples of an aqueous acid mixture can be a mixture of acetic acid and water or a mixture of methansulphonic acid and water, for instance, a mixture 3:2 (v/v) of methansulphonic acid and water.

According to the a more preferred embodiment, the acid or an aqueous acid mixture thereof is methansulphonic acid or is a mixture of methansulphonic acid and water.

According to the an again more preferred embodiment, the acid or an aqueous acid mixture thereof is methansulphonic acid.

The amount of the acid or an aqueous acid mixture thereof that can be used to carry out the step C) ranges between 0.05 and 2 molar equivalents compared to the starting compound of formula (V).

According to a preferred embodiment, to carry out the step C) from 0.05 to 0.5 molar equivalents of the acid or an aqueous acid mixture thereof.

According to a more preferred embodiment, to carry out the step C) 0.1 molar equivalents of the acid or an aqueous acid mixture thereof.

The reduction reaction of step C) is carried out in presence of a iodide catalyst and in an acid or an aqueous acid mixture thereof.

According to an embodiment, the reduction reaction of step C) is carried out by a phosphorus and/or sulphurous reductant, in presence of a iodide catalyst.

According to an embodiment, the reduction reaction of step C) is carried out by a phosphorus and/or sulphurous reductant, in presence of a iodide catalyst and in an acid or an aqueous acid mixture thereof.

According to a preferred embodiment, the reduction reaction of step C) is carried out by a phosphorus and/or sulphurous reductant, in presence of a iodide catalyst and in an acid or an aqueous acid mixture thereof which is chosen in the group comprising of hydroiodic acid, hydrobromic acid, acetic acid, methansulphonic acid, trifluoromethansulphonic acid.

According to a more preferred embodiment, the reduction reaction of step C) is carried out by a phosphorus and/or sulphurous reductant, in presence of a iodide catalyst and in an acid or an aqueous acid mixture thereof which is chosen in the group comprising of hydrobromic acid, acetic acid and methansulphonic acid.

According to a more preferred embodiment, the reduction reaction of step C) is carried out by under the following conditions: the iodine catalyst is iodine, the phosphorus and/or sulphurous reductant is phosphorous acid, and the acid or an aqueous acid mixture thereof is selected in the group comprising of hydrobromic acid, acetic acid, methansulphonic acid, being more preferred methansulphonic acid.

According to an more preferred embodiment, the reduction reaction of step C) is carried out by phosphorous acid as phosphorus and/or sulphurous reductant, in presence of a iodide catalyst and in an acid or an aqueous acid mixture thereof chosen in the group comprising of hydrobromic acid, acetic acid, and methansulphonic acid.

According to another preferred embodiment, the reduction reaction of step C) is carried out by a phosphorus and/or sulphurous reductant, in presence of a iodine as iodide catalyst and in an acid or an aqueous acid mixture thereof chosen in the group comprising of hydrobromic acid, acetic acid, and methansulphonic acid.

According to another preferred embodiment, the reduction reaction of step C) is carried out by phosphorous acid as a phosphorus and/or sulphurous reductant, in presence of a iodine as iodide catalyst.

According to an again more preferred embodiment, the reduction reaction of step C) is carried out by phosphorous acid as a phosphorus and/or sulphurous reductant, in presence of a iodine as iodide catalyst and in an acid or an aqueous acid mixture thereof chosen in the group comprising of hydrobromic acid, acetic acid, and methansulphonic acid.

According to an again more preferred embodiment, the reduction reaction of step C) is carried out by phosphorous acid as a phosphorus and/or sulphurous reductant, in presence of a iodine as iodide catalyst and in an acid or an aqueous acid mixture thereof being methansulphonic acid.

According to an embodiment of the invention, the step C) can be carried out using 0.1 molar equivalents of iodine as Iodide catalyst and 4 molar equivalents of phosphorous acid as phosphorus and/or sulphurous reductant.

According to an embodiment of the invention, the step C) can be carried out using 0.1 molar equivalents of iodine as Iodide catalyst and 4 molar equivalents of phosphorous acid as phosphorus and/or sulphurous reductant and using an acid or an aqueous acid mixture thereof.

According to a preferred embodiment of the invention, the step C) can be carried out using 0.1 molar equivalents of iodine as Iodide catalyst and 4 molar equivalents of phosphorous acid as phosphorus and/or sulphurous reductant and using methansulphonic acid as an acid or an aqueous acid mixture thereof.

In preferred embodiments, step C) is conducted at a temperature between 90° C. and 130° C. More preferably, the temperature in step C) is comprised between 100° C. and 120° C. More preferably, the temperature in step C) is 110° C.

The step C) is concluded in less than 45 hours, typically in 15-30 hours.

The step C) provides the product TFPAA of formula (II) with chemical purity of the isolated crude product of 95-99%, as determined by HPLC NA %.

The step C) provides the product TFPAA of formula (II) with chemical purity of the isolated crude product of 95-99%, typically about 98%, as determined by HPLC NA %.

The step C) provides the product TFPAA of formula (II) with the molar yield of 80-90%.

It should be noted as said molar yield of 80-90% of the direct conversion of the compound of formula (V) to the compound of formula (II) is remarkably high and that said direct conversion appears not to be described in prior art for preparing (II) starting from (V).

The chemical purity of the product TFPAA can be further increased by recrystallization of the product, for example by heating and then cooling the product within 4 volumes of toluene, thus achieving TFPAA with a chemical purity higher than 99.7%, typically about 99.8%, as determined by HPLC A/A %.

According to a more preferred embodiment, the step C) can be carried out using the iodide catalyst is in the amount between 0.05 and 0.5 molar equivalents compared to the compound of formula (V), the phosphorus and/or sulphurous reductant is in the amount between 1.5 and 8 molar equivalents compared to the compound of formula (V), and the acid or an aqueous acid mixture thereof in the amount between 0.05 and 2 molar equivalents compared to the compound of formula (V).

According to another embodiment of the invention, the step C) can be carried out using from 0.05 to 0.2 molar equivalents of iodine as Iodide catalyst and from 3 to 6 molar equivalents of phosphorous acid as phosphorus and/or sulphurous reductant and using, as an acid or an aqueous acid mixture thereof, methansulphonic acid.

According to a more preferred embodiment of the invention, the step C) can be carried out using from 0.05 to 0.2 molar equivalents of iodine as Iodide catalyst and from 3 to 6 molar equivalents of phosphorous acid as phosphorus and/or sulphurous reductant and using, as an acid or an aqueous acid mixture thereof, from 0.05 to 0.3 equivalent of methansulphonic acid. This combination of conditions provides indeed highest molar yield and highest chemical purity of the product TFPAA.

According to an again more preferred embodiment of the invention, the step C) can be carried out using 0.1 molar equivalents of iodine as Iodide catalyst and 4 molar equivalents of phosphorous acid as phosphorus and/or sulphurous reductant and using, as an acid or an aqueous acid mixture thereof, 0.1 equivalent of methansulphonic acid. This combination of conditions provides indeed best molar yield and best chemical purity of the product TFPAA.

According to another embodiment of the invention, the step C) can be carried out using 0.1 molar equivalents of iodine as Iodide catalyst and 4 molar equivalents of phosphorous acid as phosphorus and/or sulphurous reductant and using, as an acid or an aqueous acid mixture thereof, 0.1 molar equivalents of methansulphonic acid.

According to a preferred embodiment, whichever is the catalyst or the reductant, the step C) is carried out in absence of water, since it provides higher molar yield of the product of formula (II), compared with conditions wherein water is present.

According to a more preferred embodiment, the step C) is carried out in absence of water and is carried out by phosphorous acid as a phosphorus and/or sulphurous reductant, in presence of a iodine as iodide catalyst and in an acid chosen in the group comprising of hydrobromic acid, acetic acid, and methansulphonic acid, being more preferred methansulphonic acid.

The compound 2,4,5-trifluorophenylacetic acid of formula (II) or salt thereof:

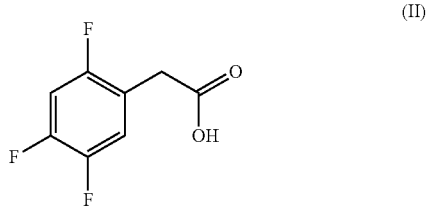 [SMILES: O=C(O)Cc1cc(F)c(F)cc1F]

can be thus prepared by the following steps:

A) cyanation of 2,4,5-trifluorobenzoyl fluoride of formula (III):

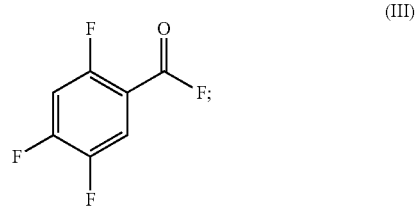 [SMILES: O=C(F)c1cc(F)c(F)cc1F]

to give the compound of formula (IV):

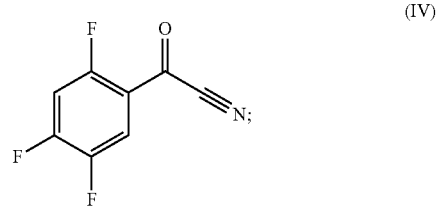 [SMILES: N#CC(=O)c1cc(F)c(F)cc1F]

B) conversion of the compound of formula (IV) prepared in the step A) to the compound of formula (V):

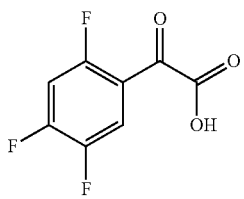

(V)

C) reduction of the compound of formula (V) prepared in the step B) to the compound of formula (II):

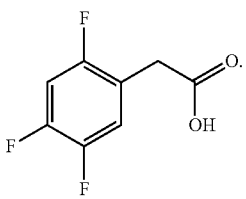

(II)

Moreover, the condition discussed above to carry out the step A), B) and C) also apply to said preparation of TFPAA of formula (II) starting from the compound of formula (III).

In particular, said cyanation reaction (of step A)) is carried out in presence cyanide source. More particularly, the cyanation reaction of step A) can be preferably carried out in presence of sodium cyanide.

In particular, said conversion reaction (of step B)) can be carried out in presence alkali metal halide. More particularly, the conversion reaction of step B) can be preferably carried out in presence of sodium chloride.

In particular, said reduction reaction (of step C)) can be carried out in presence of iodide catalyst and with a phosphorus and/or sulphurous reductant and is carried out in an acid or an aqueous acid mixture thereof.

More particularly, the reduction reaction of step C) can be carried out in presence of iodine, with phosphorous acid and methansulphonic acid.

The compound 2,4,5-trifluorophenylacetic acid of formula (II) or salt thereof:

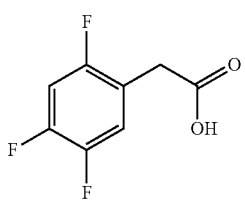

(II)

can be thus prepared by direct conversion of the compound of (V):

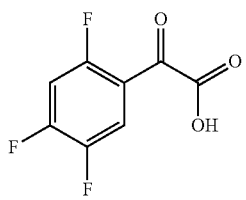

(V)

to the compound of formula (II), wherein said direct conversion is carried out by reduction reaction.

Moreover, the condition discussed above to carry out the step C) also apply to said preparation of TFPAA of formula (II) starting from the compound of formula (V).

In particular, said reduction reaction (of step C)) can be carried out in presence of iodide catalyst and with a phosphorus and/or sulphurous reductant and is carried out in an acid or an aqueous acid mixture thereof.

More particularly, the reduction reaction of step C) can be preferably carried out in presence of iodine, with phosphorous acid and methansulphonic acid.

A phosphorus and/or sulphurous reductant, particularly phosphorous acid, or a iodide catalyst, particularly iodine, or methansulphonic acid can be thus used to carry out the conversion of the compound of formula (V):

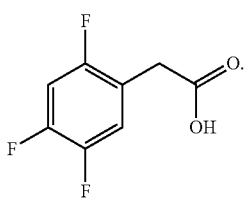

(V)

to 2,4,5-trifluorophenylacetic acid of formula (II) or salt thereof:

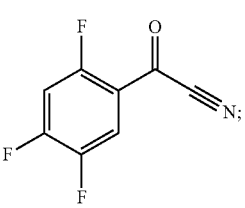

(II)

The compound of formula (IV):

(IV)

or compound of formula (V):

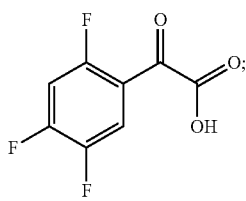

can be used for the preparation of the 2,4,5-trifluorophenylacetic acid of formula (II) or salt thereof:

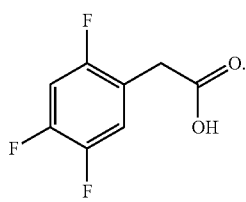

In one embodiment of the present invention, Sitagliptin of formula (I) or salt thereof, prepared according to the above process, may be included in pharmaceutical compositions, comprising one or more pharmaceutically acceptable excipients or in combination with other active pharmaceutical ingredients and one or more pharmaceutically acceptable excipients.

Example of suitable pharmaceutical composition, in particular in combination with other active pharmaceutical ingredients, is a tablet comprising 50 mg of Sitagliptin (as phosphate monohydrate salt) and 850 mg of metformin hydrochloride.

Other examples suitable pharmaceutical compositions are following described:
  25 mg tablet contains sitagliptin phosphate monohydrate, equivalent to 25 mg sitagliptin,
  50 mg tablet contains sitagliptin phosphate monohydrate, equivalent to 50 mg sitagliptin,
  100 mg tablet contains sitagliptin phosphate monohydrate, equivalent to 100 mg sitagliptin,
wherein the above pharmaceutical compositions contain the following excipients in tablet core: microcrystalline cellulose (E460), calcium hydrogen phosphate, anhydrous (E341), croscarmellose sodium (E468), magnesium stearate (E470b) and sodium stearyl fumarate.

Furthermore the film coating of the said pharmaceutical compositions can be made up the following excipients: poly(vinyl alcohol), macrogol 3350, talc (E553b), titanium dioxide (E171), red iron oxide (E172) and yellow iron oxide (E172).

All the features and preferred embodiments of the process of the present invention given above can be combined in each possible combination to carry out the claimed process.

All of the intermediates and compounds of the present invention in particular those of formula (II), (III), (IV), (V) can be in isolated or in not isolated form, from the reaction mixture wherein they are prepared.

According to the preferred embodiment, all of the intermediates and compounds isolated are typically in form of a solid or of an isolated oil.

According to the preferred embodiment, all of the intermediates and compounds not isolated are typically in form of solution with an organic solvent or water.

The skilled in the art of organic chemistry can appreciate as the process of the invention allows an improvement of the productivity considering the reductions of number of steps employed to carry out the synthesis of Sitagliptin, and, at the same time, avoiding the use of expensive reagents.

The term "volume" means volume of solvent per unit of product, thus, for example, 1 volume is 1 Liter per 1 Kilo, or 1 mL for 1 gram, or 1 microliter per 1 milligram. Thus, 10 volumes means for example 10 liters per 1 Kilogram of substance.

EXPERIMENTAL SECTION

The starting material 2,4-Dichloro-5-fluorobenzoyl chloride, is a reactant largely commercially available, for example, as supplied by Alfa Aesar (USA).

The starting material Triazole having the following formula or the hydrocloride salt:

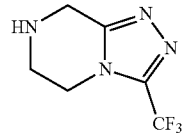

used for the synthesis of Ketoamide of formula (IV) in the step F), is reactants largely commercially available, for example, supplied by Alfa Aesar (Germany), Toronto Research Chemicals Product List, abcr GmbH Product List, Sigma-Aldrich (USA).

A few methods for the preparation of Triazole have been described, for example, Jaume Balsellsin at all in Organic Letters, 7 (6), 1039-1042, 2005 described the synthesis of [1,2,4]Triazolo[4,3-r]piperazines via condensation of high reactive chloromethyloxadiazoles with ethylenediamins.

Alternatively, WO2004/080958 described, in the example 1, in particular Step D, the preparation of 3-(trifluoromethyl)-5,6,7,8-tetrahydro[1,2,4]triazolo[4,3-a]pyrazine, hydrochloride salt (1-4).

Moreover, the synthesis of Triazole is described in the steps from A to D C, related to scheme 1, at pag 32 of WO2007/050485.

Volumes means volume of solvent per unit of product, thus, for example, 1 volume is 1 Liter per 1 Kilo, or 1 mL for 1 gram, or 1 microliter per 1 milligram. Thus, 10 volumes means for example 10 liters per 1 Kilogram of substance.

Example 1: Preparation of 2,4,5-trifluorobenzoyl fluoride, Compound (III)

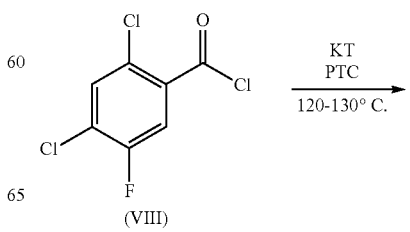

-continued

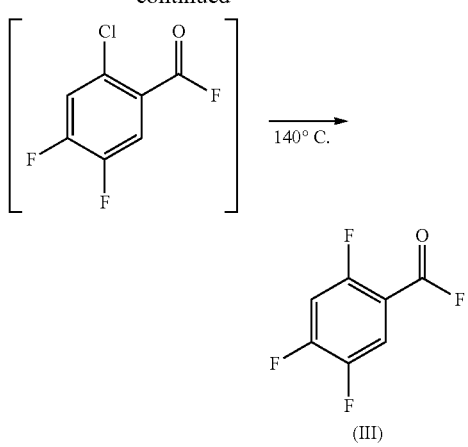

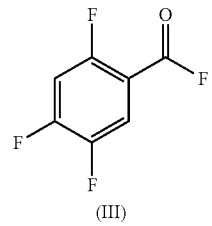
(III)

A 250 mL 4-necks round-bottom flask was charged, under nitrogen atmosphere, with 120 mL of o-dichlorobenzene (3 V), 42.8 g of Potassium Fluoride (4.2 eq.), 4 g of Tetraphenylphosphonium bromide (10% w/w compared to 2,4-Dichloro-5-fluorobenzoyl chloride), 2 g of 18-crown-6 (5% w/w compared to 2,4-Dichloro-5-fluorobenzoyl chloride), and 40 g of 2,4-Dichloro-5-fluorobenzoyl chloride of formula (VIII). The obtained mixture was heated to 120-130° C., and the mixture was stirred at this temperature for 15 hours. Then the temperature was up to 140° C. and the mixture was stirred at this temperature for further 8 hours. Once the conversion is completed (control by GC; conversion to 2,4-Dichloro-5-fluorobenzoyl chloride <0.5%). The obtained reaction mixture was concentrate on vacuum. A colourless solution of 2,4,5-trifluorobenzoyl fluoride in o-dichlorobenzene (144.4 g, 17.4% w/w) was obtained with a purity of 98% (GC NA %), by an GC external standard method, yield of 80.2%. Optionally, the product can be further purified by distillation.

Example 2: Preparation of 2,4,5-trifluorobenzoyl fluoride, Compound (III)

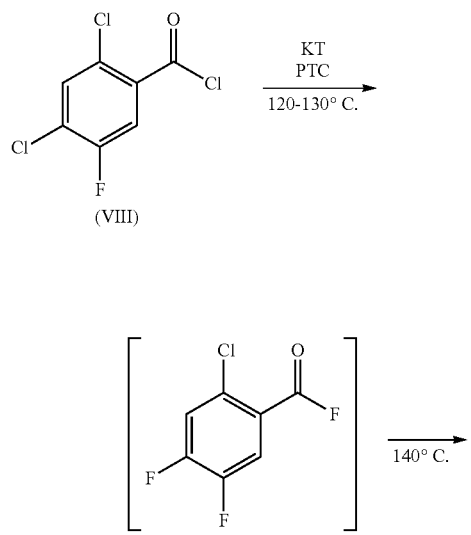

-continued

A 2 L 4-necks round-bottom flask was charged, under nitrogen atmosphere, with 600 mL of solfolane (3 V), 214 g of Potassium Fluoride (4.2 eq.), 20 g of Tetraphenylphosphonium bromide (10% w/w compared to 2,4-Dichloro-5-fluorobenzoyl chloride), 10 g of 18-crown-6 (5% w/w compared to 2,4-Dichloro-5-fluorobenzoyl chloride), and 200 g of 2,4-Dichloro-5-fluorobenzoyl chloride of formula (VIII). The obtained mixture was heated to 120-130° C., and the mixture was stirred at this temperature for 12 hours. Then the temperature was raised up to 140° C. and the mixture was stirred at this temperature for further 8 hours. Once the conversion is completed (control by GC; conversion to 2,4-Dichloro-5-fluorobenzoyl chloride <0.5%). The obtained reaction mixture was concentrate to residue, and then the residue was distilled on vacuum. A colourless oil of 2,4,5-trifluorobenzoyl fluoride (120 g) was obtained with a purity of 99.1% (GC NA %), and an yield of 76.6%.

Optionally, the product can be further purified by distillation.

Example 3: Preparation of 2,4,5-trifluorobenzene-1-carbonyl cyanide, Compound (IV)

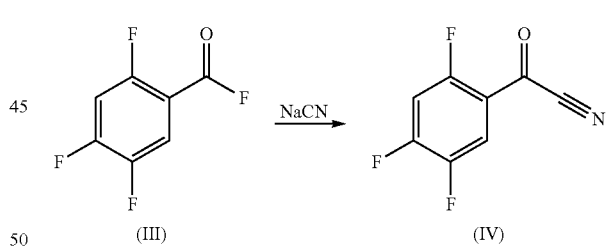

A 50 mL 4-necks round-bottom flask was charged, under nitrogen atmosphere, with 2.2 g of NaCN (1.4 eq) in 15 mL of toluene (2.6 V). The obtained mixture was heated to 110° C., and then 5.8 g of 2,4,5-trifluorobenzoyl fluoride of formula (III) was added dropwise over a period of 1 hour. The reaction mixture was stirred at these temperature for 6 hours. Once the conversion is completed (control by GC; conversion to 2,4,5-trifluorobenzoyl fluoride <1%), the mixture was cooled to temperature below 50° C. Then the reaction mixture was filtered and the filtrate was washed with 8 mL of toluene. The obtaining solution was concentrate to residue, and then the residue was distilled on vacuum. A colourless oil of 2,4,5-trifluorobenzoyl fluoride (4.94 g) was obtained with a purity of 96.6% (GC NA %), and an yield of 82%.

Example 4: Preparation of 2,4,5-trifluorobenzene-1-carbonyl cyanide, Compound (IV)

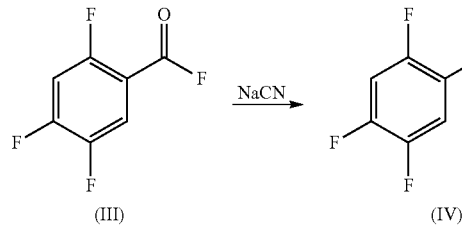

A 50 mL 4-necks round-bottom flask was charged, under nitrogen atmosphere, with 2.2 g of NaCN (1.4 eq) in 15 mL of chlorobenzene (2.6 V). The obtained mixture was heated to 110° C., and then 6 g of 2,4,5-trifluorobenzoyl fluoride of formula (III) was added dropwise over a period of 1 hour. The reaction mixture was stirred at these temperature for 6 hours. Once the conversion is completed (control by GC; conversion to 2,4,5-trifluorobenzoyl fluoride <1%), the mixture was cooled to temperature below 50° C. Then the reaction mixture was filtered and the filtrate was washed with 8 mL of chlorobenzene. The obtaining solution was concentrate to residue, and then the residue was distilled on vacuum. A colourless oil of 2,4,5-trifluorobenzoyl fluoride (4.93 g) was obtained with a purity of 98% (GC NA %), and an yield of 79%.

Example 5: Preparation of 2,4,5-trifluorobenzene-1-carbonyl cyanide, Compound (IV)

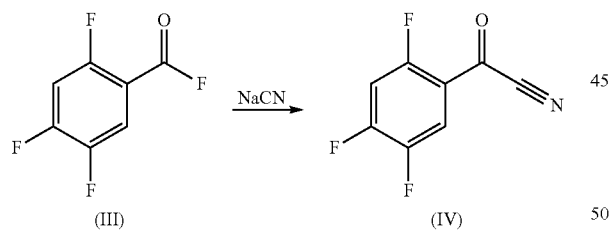

A 250 mL 4-necks round-bottom flask was charged, under nitrogen atmosphere, with 10 g of NaCN (1.4 eq) in 70 mL of 0-dichlorobenzene. The obtained mixture was heated to 110° C., and then a solution of 2,4,5-trifluorobenzoyl fluoride of formula (III) obtained in the example 1 was added dropwise over a period of 1 hour. The reaction mixture was stirred at these temperature for 6 hours. Once the conversion is completed (control by GC; conversion to 2,4,5-trifluorobenzoyl fluoride <1%), the mixture was cooled to temperature below 50° C. Then the reaction mixture was filtered and the filtrate was washed with 8 mL of chlorobenzene. The obtaining solution was concentrate to residue, and then the residue was distilled on vacuum. A colourless oil of 2,4,5-trifluorobenzoyl fluoride (22.2 g) was obtained with a purity of 97.8% (GC NA %), and an yield of 85%.

Example 6: Preparation of 2-oxo-2-(2,4,5-trifluorophenyl)acetamide, Compound (IX)

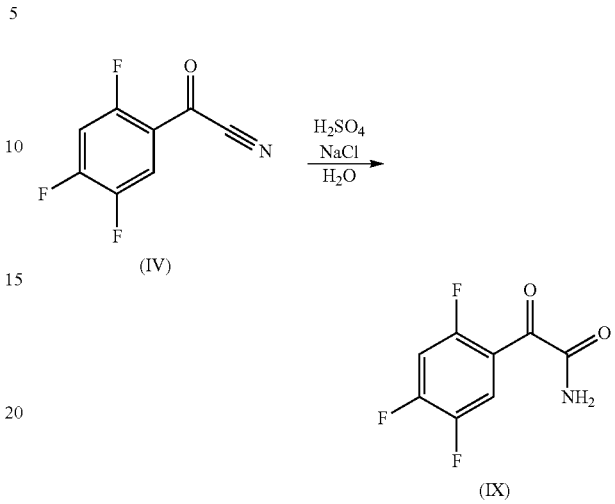

A 25 mL 4-necks round-bottom flask was charged, under nitrogen atmosphere, with 0.39 g of water (1 eq), 0.13 g of NaCl (0.1 eq) in 2.12 g of 98% $H_2SO_4$. To the obtained mixture was added dropwise over 20 min. at 20° C., 4 g of 2,4,5-trifluorobenzene-1-carbonyl cyanide of formula (IV). The reaction mixture was stirred at these temperature for 8 hours. Once the conversion is completed (control by GC), the mixture was added to a 10 mL of ice-water. The obtaining mixture was stirred for 30 min., then the obtained suspension was filtered and the filtrate was washed with 10 mL of water. A solid of 2-oxo-2-(2,4,5-trifluorophenyl)acetamide of formula (IX) (4.1 g) was obtained, yield of 93.4%.

Optionally, the product can be further purified by crystallization from methyl-tertbutyl ether.

Example 7: Preparation of (2,4,5-trifluorophenyl)oxoacetic acid, Compound (V)

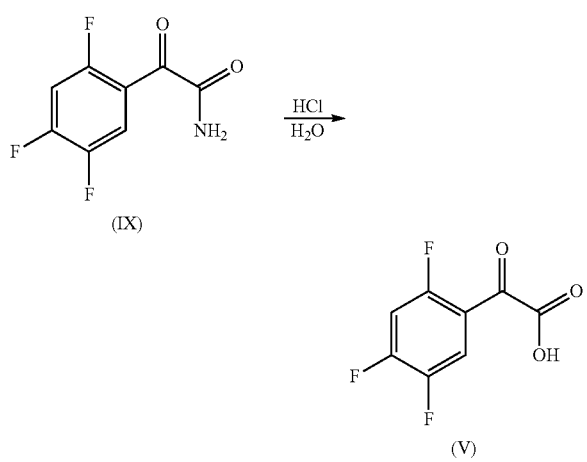

A 25 mL 4-necks round-bottom flask was charged, under nitrogen atmosphere, with 4 g of 2-oxo-2-(2,4,5-trifluorophenyl)acetamide of formula (IX) in 20 mL of 36% HCl. To the obtained reaction mixture was heated to 70° C. and was stirred at these temperature for 5 hours. Once the conversion is completed (control by HPLC), the mixture was cooled to r.t. and 10 mL of MTBE was added. The obtained mixture was stirred for 5 min., then the organic layers were separated. Then 10 mL of methyl tert-butyl ether was added to the aqueous layers, stirred for 5 min, then the phase were separated. The organic layer were combined and then the combined organic phase was concentrated under vacuum at 35° C., to provide the crude (2,4,5-trifluorophenyl)oxoacetic acid of formula (V), 3.35 g, molar yield 83.4%, chemical purity HPLC NA % 99.60%.

Optionally, the obtained crude (2,4,5-trifluorophenyl) oxoacetic acid of formula (V) can be further purified by recrystallized from toluene.

Example 8: Preparation of (2,4,5-trifluorophenyl)oxoacetic acid, Compound (V)

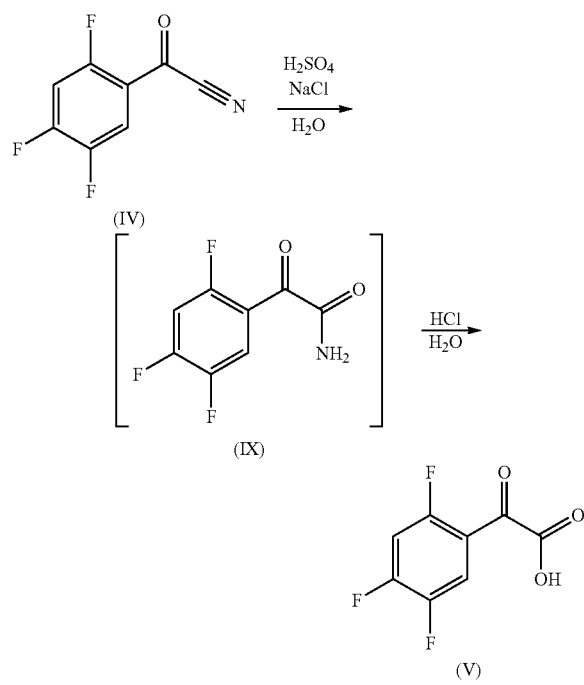

A 25 mL 4-necks round-bottom flask was charged, under nitrogen atmosphere, with 0.39 g of water (1 eq), 0.13 g of NaCl (0.1 eq) in 2.12 g of 98% $H_2SO_4$. To the obtained mixture was added dropwise over 20 min. at 20° C., 4 g of 2,4,5-trifluorobenzene-1-carbonyl cyanide of formula (IV). The reaction mixture was stirred at these temperature for 8 hours. Once the conversion is completed (control by GC), the mixture was added to a 10 mL of ice-water. The obtaining mixture was stirred for 30 min., then the obtained suspension was filtered. The obtained filtrate was suspended in 20 mL of 36% HCl, and then the reaction mixture was heated to 70° C. for 5 hours. Once the conversion is completed (control by HPLC), the mixture was cooled to r.t. and 10 mL of MTBE was added. The obtained mixture was stirred for 5 min., then the organic layers were separated. Then 10 mL of methyl tert-butyl ether was added to the aqueous layers, stirred for 5 min, then the phase were separated. The organic layer were combined and then the combined organic phase was concentrated under vacuum at 35° C., to provide the crude (2,4,5-trifluorophenyl)oxoacetic acid of formula (V), 3.75 g, molar yield 85%, chemical purity HPLC A/A % 99.30%.

Optionally, the obtained crude (2,4,5-trifluorophenyl) oxoacetic acid of formula (V) can be further purified by recrystallized from toluene.

Example 9: Preparation of (2,4,5-trifluorophenyl)oxoacetic acid, Compound (V)

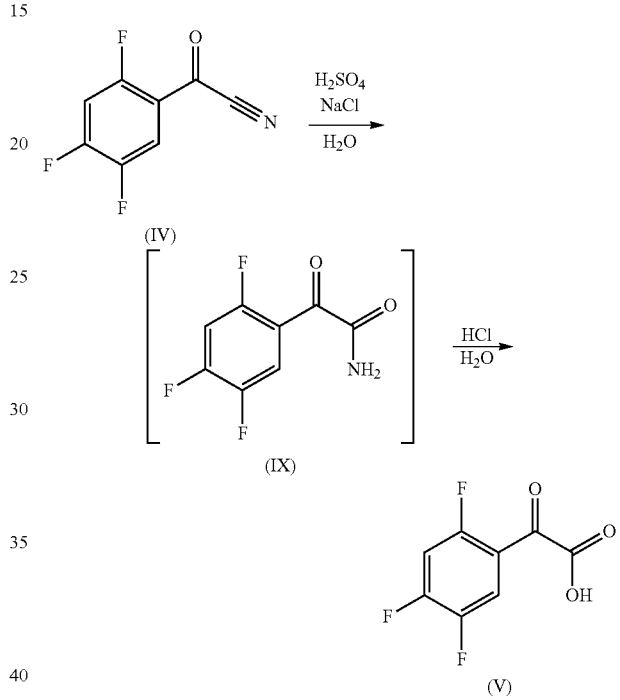

A 25 mL 4-necks round-bottom flask was charged, under nitrogen atmosphere, with 0.39 g of water (1 eq), 0.22 g of NaBr (0.1 eq) in 2.12 g of 98% $H_2SO_4$. To the obtained mixture was added dropwise over 20 min. at 20° C., 4 g of 2,4,5-trifluorobenzene-1-carbonyl cyanide of formula (IV). The reaction mixture was stirred at these temperature for 8 hours. Once the conversion is completed (control by GC), the mixture was added to a 10 mL of ice-water. The obtaining mixture was stirred for 30 min., then the obtained suspension was filtered. The obtained filtrate was suspended in 20 mL of 36% HCl, and then the reaction mixture was heated to 70° C. for 5 hours. Once the conversion is completed (control by HPLC), the mixture was cooled to r.t. and 10 mL of MTBE was added. The obtained mixture was stirred for 5 min., then the organic layers were separated. Then 10 mL of methyl tert-butyl ether was added to the aqueous layers, stirred for 5 min, then the phase were separated. The organic layer were combined and then the combined organic phase was concentrated under vacuum at 35° C., to provide the crude (2,4,5-trifluorophenyl)oxoacetic acid of formula (V), 3.75 g, molar yield 85%, chemical purity HPLC A/A % 99.30%.

Optionally, the obtained crude (2,4,5-trifluorophenyl) oxoacetic acid of formula (V) can be further purified by recrystallized from toluene.

Example 10: Preparation of 2,4,5-Trifluorophenylacetic acid, compound (II)

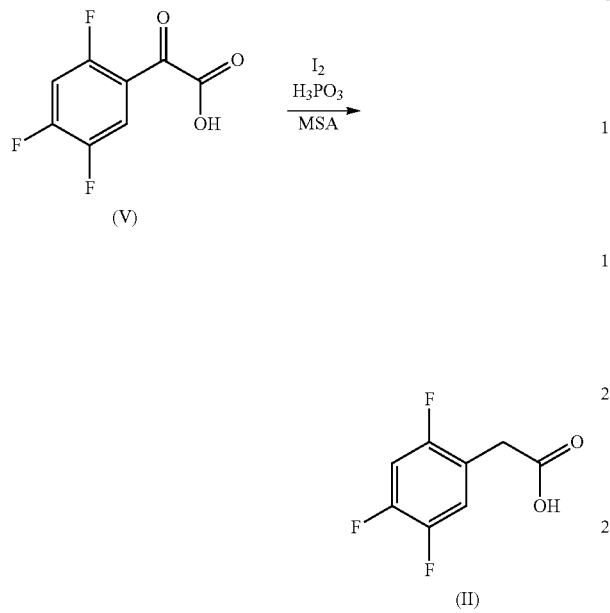

A 25 mL flask was charged with 1.0 g of (2,4,5-trifluorophenyl)oxoacetic acid (compound of formula (V)), 1.61 g of $H_3PO_3$ (4 eq.), 0.12 g of $I_2$ (0.1 eq.) and 0.05 g of methanesulfonic acid (0.1 eq.) (abbreviated MSA). The obtained mixture was stirred at 110° C. for 24 hours. Once the conversion is completed (by HPLC; conversion >99%), the mixture is cooled to temperature below 30° C., then, and 5 mL of methyl tert-butyl ether were added and then, 5 mL of water were added. The obtained mixture was stirred for 5 min., then the organic layers were separated. Then 5 mL of methyl tert-butyl ether was added to the aqueous layers, stirred for 5 min, then the phase were separated. The organic layer were combined, and then the combined organic layers was concentrated under vacuum at 35° C., to provide the crude TFPAA (of formula (II)), 0.77 g, molar yield 83%, chemical purity HPLC A/A % 98.9%.

Optionally, the obtained crude TFPAA can be further recrystallized from

Example 11: Preparation of 4-oxo-4-[3-(trifluoromethyl)-5,6-dihydro[1,2,4]triazolo[4,3-a]pyrazin-7(8H)-yl]-1-(2,4,5-trifluorophenyl)butan-2-one, Compound (VI)

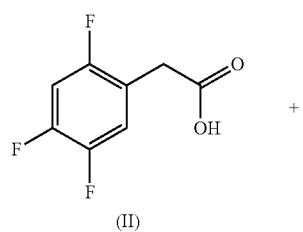

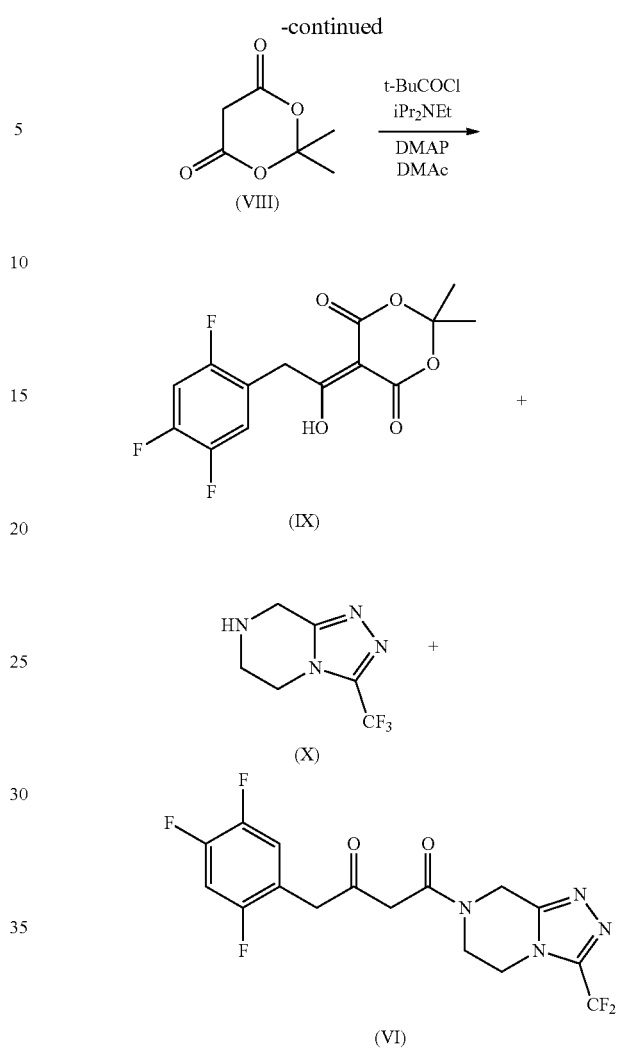

A 5 L 4-necks round-bottom flask was charged, under nitrogen atmosphere, with 2,4,5-Trifluorophenylacetic acid (II) (150 g, 0.789 mol), Meldrum's acid (VIII) (125 g, 0.868 mol), and 4-(dimethylamino)pyridine (DMAP) (7.7 g, 0063 mol). N,N-Dimethylacetamide (DMAc) (525 mL) was added in one portion at room temperature to dissolve the solids. N,N-diisopropylethylamine (282 mL, 1.62 mol) was added in one portion at room temperature while maintaining the temperature below 40° C. Pivaloyl chloride (107 mL, 0.868 mol) was added dropwise aver 2 h while maintaining the temperature below 5° C. The reaction mixture was aged at 5° C. for 1 h. Triazale hydrochloride (X) (180 g, 0.789 mal) was added at the same temperature. The reaction solution was aged at 70° C. for 6 h. Then 5% Aqueous sodium hydrogen carbonate solution (625 mL) was added at 20-45° C. The mixture was aged at 20-30° C. for 2 h. Then 525 mL of 5% aqueous sodium hydrogen carbonate solution was added over 3 h. After aging for 4 hours at room temperature, the slurry was cooled to 0-5° C. and aged 1 h before filtering the solid. The wet cake was washed with 20% aqueous DMAc (300 mL), followed by an additional twice with 20% aqueous DMAc (400 mL), and finally with water (400 mL). The cake was dried at room temperature.

Example 12: Preparation of (2Z)-4-oxo-4-[3-(trifluoromethyl)-5,6-dihydra[1,2,4]triazalo[4,3-a]pyrazin-7(8H)-yl]-1-(2,4,5-trifluorophenyl)but-2-en-2-amine, Compound (VII)

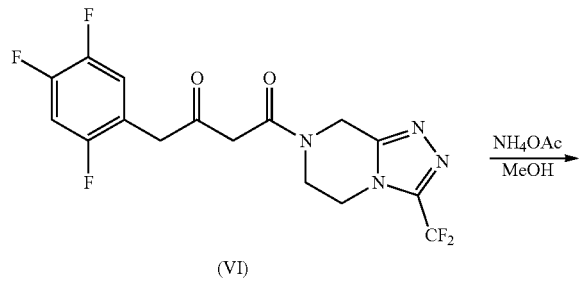

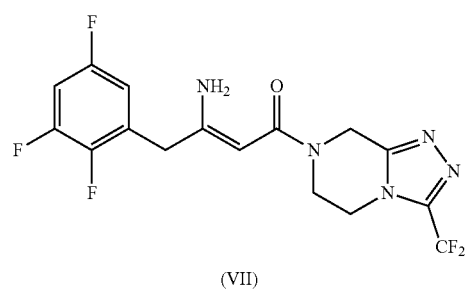

A 2 L round-bottom flask was charged with methanol (100 mL), the ketoamide (VI) (200 g), and ammonium acetate (110.4 g). Methanol (180 mL) and 28% aqueous ammonium hydroxide (58.6 mL) were then added keeping the temperature below 30° C. during the addition. Additional methanol (100 mL) was added to the reaction mixture. The mixture was heated at reflux temperature and aged for 2 h. The reaction was cooled to room temperature and then to about 5° C. After 30 min, the solid was filtered and dried to afford obtained Enamine Amide of formula (VII) as a solid; m.p. 271.2° C.

Example 13: Preparation of (2R)-4-axa-4-[3-(trifluoromethyl)-5,6-dihydro[1,2,4]triazalo[4,3-a]pyrazin-7(8H)-yl]-I-(2,4,5-trifluorophenyl)butan-2-amine, Sitagliptine, Compound (I)

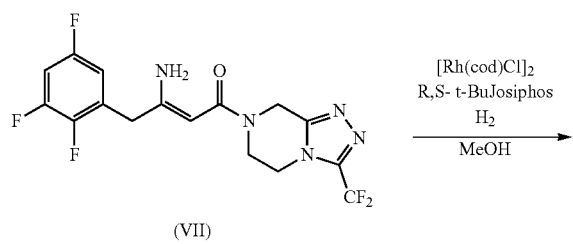

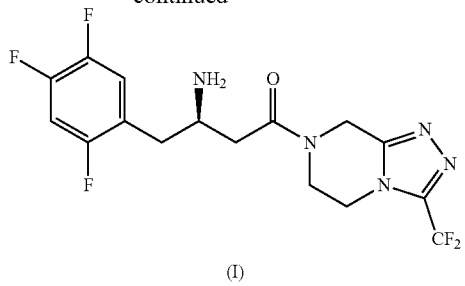

Into a 500 ml flask were charged chloro(1,5-cyclooctadiene)rhodium(I) dimer {[Rh(cod)Cl]$_2$} (292 mg, 1.18 mmol) and (R,S) t-butyl Josiphos (708 mg, 1.3 mmol) under a nitrogen atmosphere. Degassed MeOH was then added (200 mL) and the mixture was stirred at room temperature for 1 h. Into a 4 L hydrogenator was charged the enamine amide (VII) (118 g, 0.29 mal), MeOH (1 L). The catalyst solution was then transferred to the hydrogenator. After degassing three times, the enamine amide was hydrogenated under 200 psi hydrogen at 50° C. for 13 h. The obtained methanol solution was concentrated and switched to methyl t-butyl ether (MTBE) (45 mL). Into this solution was added aqueous H$_3$PO$_4$ solution (0.5 M, 95 mL). After separation of the layers, 3N NaOH (35 mL) was added to the water layer, which was then extracted with MTBE (180 mL+100 mL). The MTBE solution was concentrated and solvent switched to hot toluene (180 mL, about 75° C.). The toluene solution was then cooled to 0° C. The crystals were isolated by filtration to obtained Sitagliptin (I) (13 g, yield 72%, 98-99% ee); m.p. 114.1-115.7° C. 1HNMR (300 MHz, CD3CN): 7.26 (m), 7.08 (m), 4.90 (s), 4.89 (s), 4.14 (m), 3.95 (m), 3.40 (m), 2.68 (m), 2.49 (m), 1.40 (bs). 13CNMR (CD3CN): 171.8, 157.4, 152.2, 151.8, 149.3, 147.4, 144.2, 124.6, 120.4, 119.8, 106.2, 50.1, 44.8, 44.3, 43.2, 42.4, 41.6, 41.4, 39.6, 38.5, 36.9.

Example 14: Analytical Method to Analyse 2,4,5-Trifluorophenylacetic Acid

Determination of Purity, Impurity Profile and Assay by HPLC:
Chromatographic Conditions:

| Column: | Water Symmetry C18, 250 × 4.6 mm, 5 μm particle diameter | | |
|---|---|---|---|
| Mobile phase A: | 0.1% phosphoric acid (85%) | | |
| Mobile Phase B: | acetonitrile | | |
| Gradient: | Time (min) | % A | % B |
| | 0 | 90 | 10 |
| | 10 | 65 | 35 |
| | 30 | 20 | 80 |
| | 35 | 20 | 80 |
| Detector: | UV at 210 nm | | |
| Flow Rate: | 1.0 mL/min. | | |
| Column Temperature: | 20° C. | | |
| Injection volume: | 2 μL for IPC; 10 μL (solid: 0.2 mg /ml) | | |
| Run time: | 35 minutes | | |
| Equilibration time: | 7 minutes | | |
| Diluent: | Mobile phase A/ Mobile phase B 50/50 (v/v) | | |

The present method has been used to determinate the chemical purity of 2,4,5-Trifluorophenylacetic acid (compound (II)).

The invention claimed is:

1. A process for the preparation of Sitagliptin of formula (I) or salt thereof:

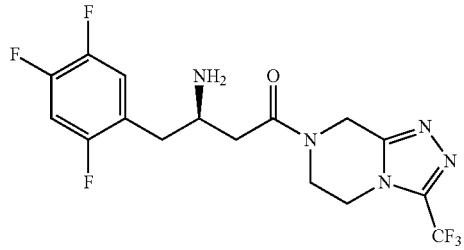

comprising:

A) cyanation of 2,4,5-trifluorobenzoyl fluoride of formula (III):

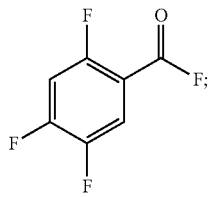

to give the compound of formula (IV):

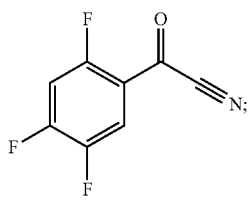

B) conversion of the compound of formula (IV) prepared in step A) to the compound of formula (V):

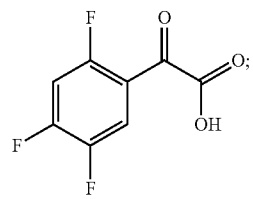

C) reduction of the compound of formula (V) prepared in step B) to the compound of formula (II):

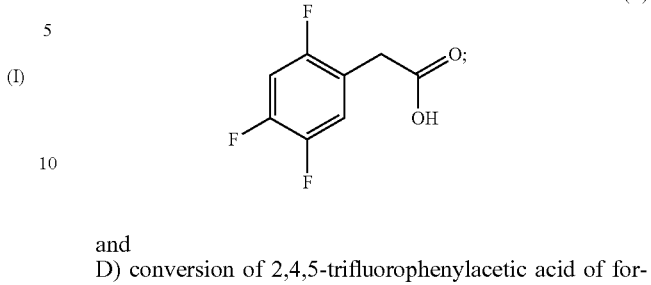

and

D) conversion of 2,4,5-trifluorophenylacetic acid of formula (II) obtained in step C) to Sitagliptin of formula (I) or salt thereof.

2. The process according to claim 1, wherein step D) is carried out by means of:

E) conversion of 2,4,5-trifluorophenylacetic acid of formula (II) obtained in step C) to Ketoamide of formula (VI):

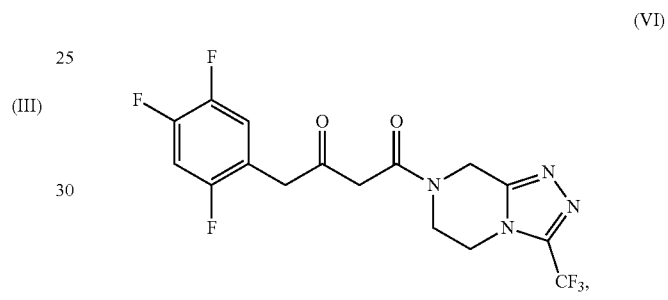

F) amination reaction of Ketoamide of formula (VI) produced in step E) to give Enamine Amide of formula (VII): and

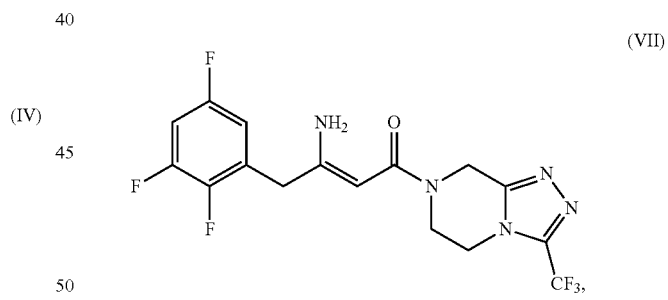

G) conversion of Enamine Amide of formula (VII) obtained in step F) to Sitagliptin of formula (I):

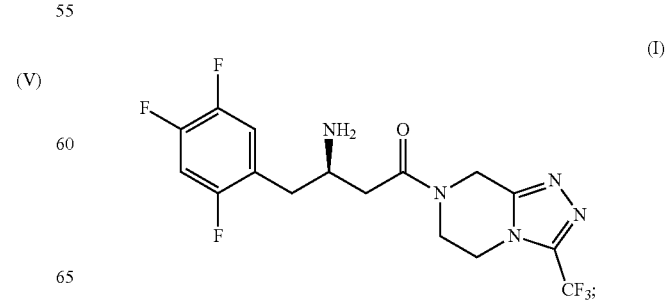

or by means of an alternative method for obtaining Sitagliptin of formula (I) consisting of:

D1) enzymatic conversion of Ketoamide of formula (VI), obtained in step E), to Sitagliptin of formula (I):

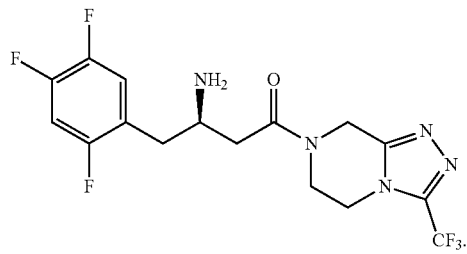

3. The process according to claim 1, wherein the conversion of step B) is carried out in presence of alkali metal halide.

4. The process according to claim 1, wherein the conversion reaction of step B) is carried out in an acid solvent or an aqueous acid mixture thereof.

5. The process according to claim 1, wherein the reduction on the step C) is carried out by means a direct conversion of the compound of (V):

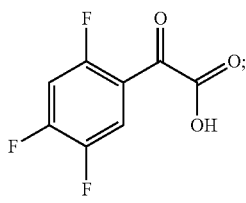

to the compound of formula (II):

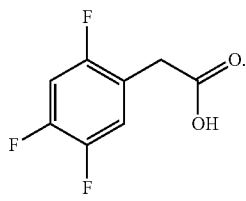

6. The process according to claim 1, wherein the reduction reaction of step C) is carried out in presence of iodide catalyst.

7. The process according to the claim 6, wherein the iodide catalyst is selected from the group consisting of iodine, sodium iodide, potassium iodide, hydroiodic acid, lithium iodide, and ammonium iodide.

8. The process according to claim 7, wherein the reduction reaction of step C) is carried out in presence of iodide catalyst and with a phosphorus and/or sulphurous reductant and is carried out in an acid or an aqueous acid mixture thereof.

9. The process according to the claim 8, wherein the iodide catalyst is sodium iodide, the phosphorus and/or sulphurous reductant is phosphorous acid, and the acid or an aqueous acid mixture thereof is selected from the group consisting of hydrobromic acid, acetic acid and methansulphonic acid.

10. The process according to claim 8, wherein the iodide catalyst is in the amount between 0.05 and 0.5 molar equivalents compared to the compound of formula (V), the phosphorus and/or sulphurous reductant is in the amount between 1.5 and 8 molar equivalents compared to the compound of formula (V), and the acid or an aqueous acid mixture thereof in the amount between 0.05 and 2 molar equivalents compared to the compound of formula (V).

11. A process for the preparation of 2,4,5-trifluorophenylacetic acid of formula (II) or salt thereof:

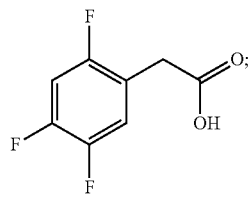

comprising:

A) cyanation of 2,4,5-trifluorobenzoyl fluoride of formula (III):

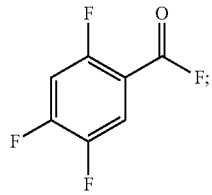

to give the compound of formula (IV):

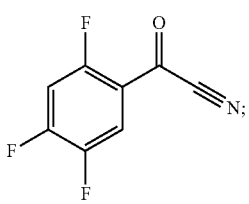

B) conversion of the compound of formula (IV) prepared in the step A) to the compound of formula (V):

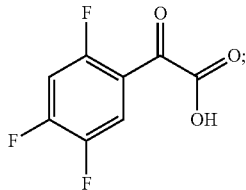
(V)

C) reduction of the compound of formula (V) prepared in the step B) to the compound of formula (II):

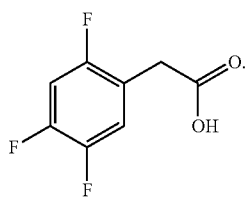
(II)

12. A process for the preparation of 2,4,5-trifluorophenylacetic acid of formula (II) or salt thereof:

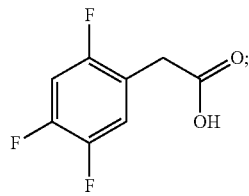
(II)

by direct conversion of the compound of (V):

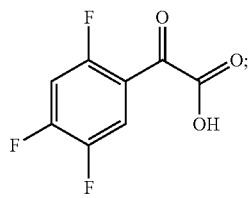
(V)

to the compound of formula (II), wherein said direct conversion is carried out by reduction reaction.

* * * * *